United States Patent [19]

Tamaki et al.

[11] 3,969,468

[45] July 13, 1976

[54] 2-AMINO-1,2,3,4-TETRAHYDRONAPHTHALENE DERIVATIVES

[75] Inventors: Kentaro Tamaki; Kyoichi Fujii; Seiichi Yada, all of Sakai; Shiro Kudo, Tokyo, all of Japan

[73] Assignee: Kyowa Hakko Kogyo Co., Ltd., Japan

[22] Filed: Oct. 29, 1973

[21] Appl. No.: 410,443

[30] Foreign Application Priority Data

Oct. 31, 1972  Japan............................. 47-108408
Oct. 31, 1972  Japan............................. 47-108409
Oct. 31, 1972  Japan............................. 47-109054

[52] U.S. Cl............................ 260/574; 260/293.54; 260/295 R; 260/295 S; 260/297 R; 260/340.9; 260/479 R; 260/501.18; 260/570.6; 260/571; 260/575
[51] Int. Cl.²......................................... C07C 93/14
[58] Field of Search............... 260/479 R, 574, 571, 260/340.9, 575

[56] References Cited
UNITED STATES PATENTS

| | | | |
|---|---|---|---|
| 2,112,899 | 4/1938 | Lott et al. ........................... | 260/571 |
| 3,637,740 | 1/1972 | Sarges................................. | 260/571 |
| 3,751,420 | 8/1973 | Hauck et al. ....................... | 260/571 |
| 3,836,670 | 9/1974 | Freed et al.......................... | 260/571 |

OTHER PUBLICATIONS

Olah Friedel–Crafts and Related Reactions, vol. II, pt. 1, (1964), p. 294, (1964).

Weygand Preparative Organic Chem., (1972), p. 846.

Bachman et al., Chem. Abstracts, vol. 41 (1947), p. 745e.

*Primary Examiner*—James A. Patten
*Attorney, Agent, or Firm*—Craig & Antonelli

[57] ABSTRACT

6,7-Benzomorphan derivatives, which are useful as unaddictive analgesics, are prepared from aromatic aminoketones through several steps of reactions. Most of the intermediates are new compounds. Process for preparing 2-benzyl-1,2,5,6-tetrahydropyridine derivatives which are known as intermediates for the preparation of 6,7-benzomorphan derivatives is also disclosed.

4 Claims, No Drawings

2-AMINO-1,2,3,4-TETRAHYDRONAPHTHALENE DERIVATIVES

BACKGROUND OF THE INVENTION

This invention relates to 6,7-benzomorphan derivatives. More specifically, it relates to a new process for producing 6,7-benzomorphan derivatives starting from aromatic aminoketones through several steps of reactions and through several intermediates. Most of the intermediates are new compounds. 6,7-benzomorphan derivatives which include pentazocine, phenazocine and cyclazocine are known to have an unaddictive analgesic activity.

6,7-benzomorphan derivatives which are subject of the present invention are represented by the formula

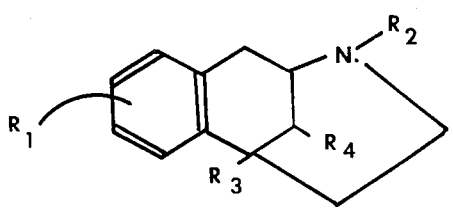

wherein $R_1$ represents a hydrogen atom, a hydroxy group, alkyl group preferably having 1 to 4 carbon atoms, such as a methyl, ethyl, isopropyl or n-butyl group, alkoxy group preferably having 1 to 4 carbon atoms, such as a methoxy, ethoxy, isopropoxy or n-butoxy group, benzyloxy group or acyloxy group preferably having 1 to 4 carbon atoms, such as a formyloxy, acetoxy, n-propionyloxy or isobutyryloxy group; $R_2$ represents a hydrogen atom, an alkyl group preferably having 1 to 8 carbon atoms, such as a methyl, ethyl, n-propyl, isobutyl, n-amyl, n-hexyl, n-heptyl or n-octyl group, substituted alkyl group (alkyl group preferably having 1 to 8 carbon atoms), the substituent being a phenyl group (for example, a benzyl or phenethyl group), benzoyl group,

group, =O group (for example, a 3-methyl carbonylpropyl group) or

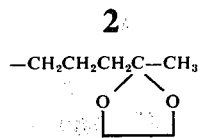

group (for example, a cycloalkyl group preferably having 3 to 6 carbon atoms, such as a cyclopropyl, cyclobutyl, cyclopentyl or cyclohexyl group, cycloalkylalkyl group preferably having 4 to 8 carbon atoms, such as a cyclopropylmethyl, cyclobutylethyl, cyclopentylmethyl, cyclohexylmethyl or 3-cyclohexylpropyl group, alkenyl group preferably having 3 to 8 carbon atoms, such as an allyl, 2-methyl-2propenyl, 2-butenyl, 3-methyl-2-butenyl or 3-methyl-3-butenyl group or substituted allkenyl group (alkenyl group preferably having 3 to 8 carbon atoms), the substituent being a halogene atom (for example, a 3-chloro-2-propenyl, 3-bromo-2-propenyl or 2,3-dichloro-2-propenyl group); and $R_3$ and $R_4$, which may be the same or different, represent alkyl groups preferably having 1 to 4 carbon atoms, such as methyl, ethyl, n-propyl or isobutyl groups.

Heretofore, there have been many reports on the processes for the preparation of 6,7-benzomorphan derivatives. These processes may be classified into four main groups of processes.

The first method employs 3,4-disubstituted pyridines as the starting material, which are converted through several steps into 2-benzyl-1,2,3,4-tetrahydropyridine derivatives and cyclized into 6,7-benzomorphan derivatives [J. Org. Chem., 24, 1432 (1959) and J. Heterocyclic Chem., 6, 43 (1959)].

The second method starts from 4-phenylpyridines. The compounds are converted into 2,4-diaxial compounds and followed by cyclization and reduction [J. Am. Chem. Soc., 90, 1064 (1968)].

The third method comprises cyclizing and reducing 2-bromo-4-(2-amino)ethyl-1-ketotetrahydronaphthalene derivatives or 1-(2-amino)ethyl-3-bromo-2-ketotetrahydronaphthalene derivatives prepared from α or β-tetralone derivatives through several intermediates [J. Chem Soc., 1947, 399 and Synthetic Analgetics, Part IIB, p. 115, Pergamon Press Ltd., Oxford (1966)].

In the fourth method, γ,δ-unsaturated alkylamines prepared from ketones and cyanoacetic acid esters are condensed with phenylacetaldehyde derivatives. The resultant 2-benzylpiperidine derivatives are cyclized into 6,7-benzomorphan derivatives [British Pat. No. 1,079,489 and J. Heterocyclic Chem., 8, 769 (1971)].

These four method are schematically illustrated below;

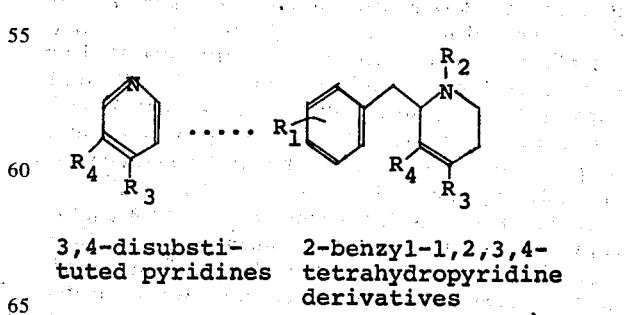

3,4-disubstituted pyridines   2-benzyl-1,2,3,4-tetrahydropyridine derivatives

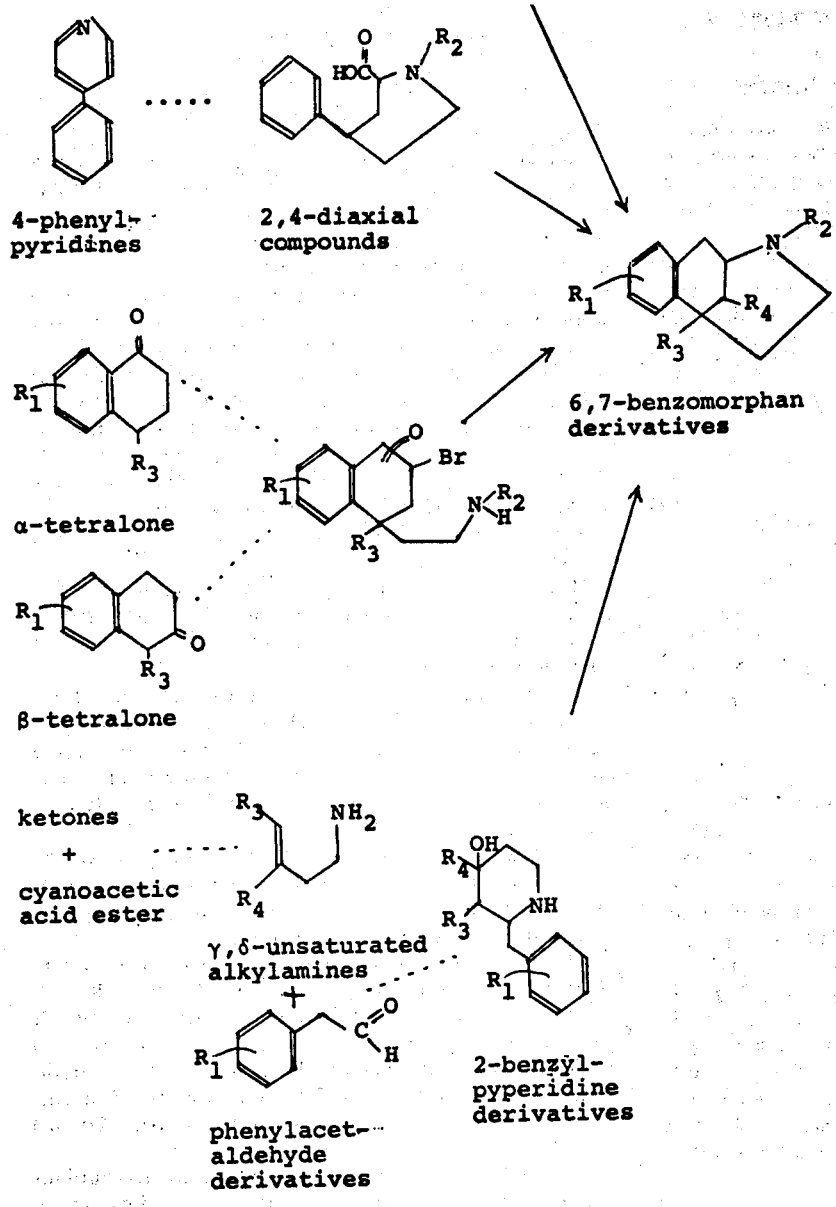

wherein $R_1$, $R_2$, $R_3$ and $R_4$ have the same significance as defined above.

However, any of these prior art processes has its own disadvantages. More specifically, in the first method, some of the intermediates are unstable. The Grignard's reaction and Stevens rearrangement reaction involved in this method result only low yields. Further, many complicated reactions are involved in the intermediate steps. Thus, the method is not practical for industrial purpose. In accordance with the second method, it is very difficult to prepare 6,7-benzomorphan derivatives having substituents at the 5 and 9 positions, which are clinically very important. The third method employs α- or β-tetralone as the starting materials, and has a difficulty in preparing 6,7-benzomorphan derivatives having a substituent at the 9 position. Further, in the fourth method, many complicated steps are involved in the preparation of the intermediate, γ,δ-unsaturated alkylamines.

In an attempt to improve the disadvantages of the prior art processes, the present inventors have made studies on the preparation of 6,7-benzomorphan derivatives. As the result, they have developed a new process, quite different from the known processes, where 6,7-benzomorphan derivatives are prepared through a series of reactions starting from aromatic aminoketones which are prepared from phenylalanine or its derivatives.

The present invention provides an advantageous process for the preparation of 6,7-benzomorphan derivatives in that the starting material is available at a low cost. Moreover, according to the present invention, 6,7-benzomorphan derivatives having various substituents at the 2, 5 and 9 positions can be obtained and the intermediates are free from unstability.

The present invention also provides a process for producing 2-benzyl-1,2,5,6-tetrahydropyridine derivatives. The compounds which are known as an intermediate in the above-mentioned first prior art method are prepared from one of the intermediates of the present process.

DESCRIPTION OF THE INVENTION

In accordance with the present invention, 6,7-benzomorphan derivatives are prepared from aromatic aminoketones through a series of reactions. First, aromatic aminoketones are reacted with organometallic compounds to prepare new compounds, 1-phenyl-2-amino-3-hexanol derivatives, which are dehydrated into 1-phenyl-2-amino-3-hexene derivatives, also new compounds. Then, the 1-phenyl-2-amino-3-hexene derivatives are cyclized into new compounds, 2-amino-1,2,3,4-tetrahydronaphthalene derivatives, which are further cyclized into 6,7-benzomorphan derivatives. These steps of reactions are schematically described as follows:

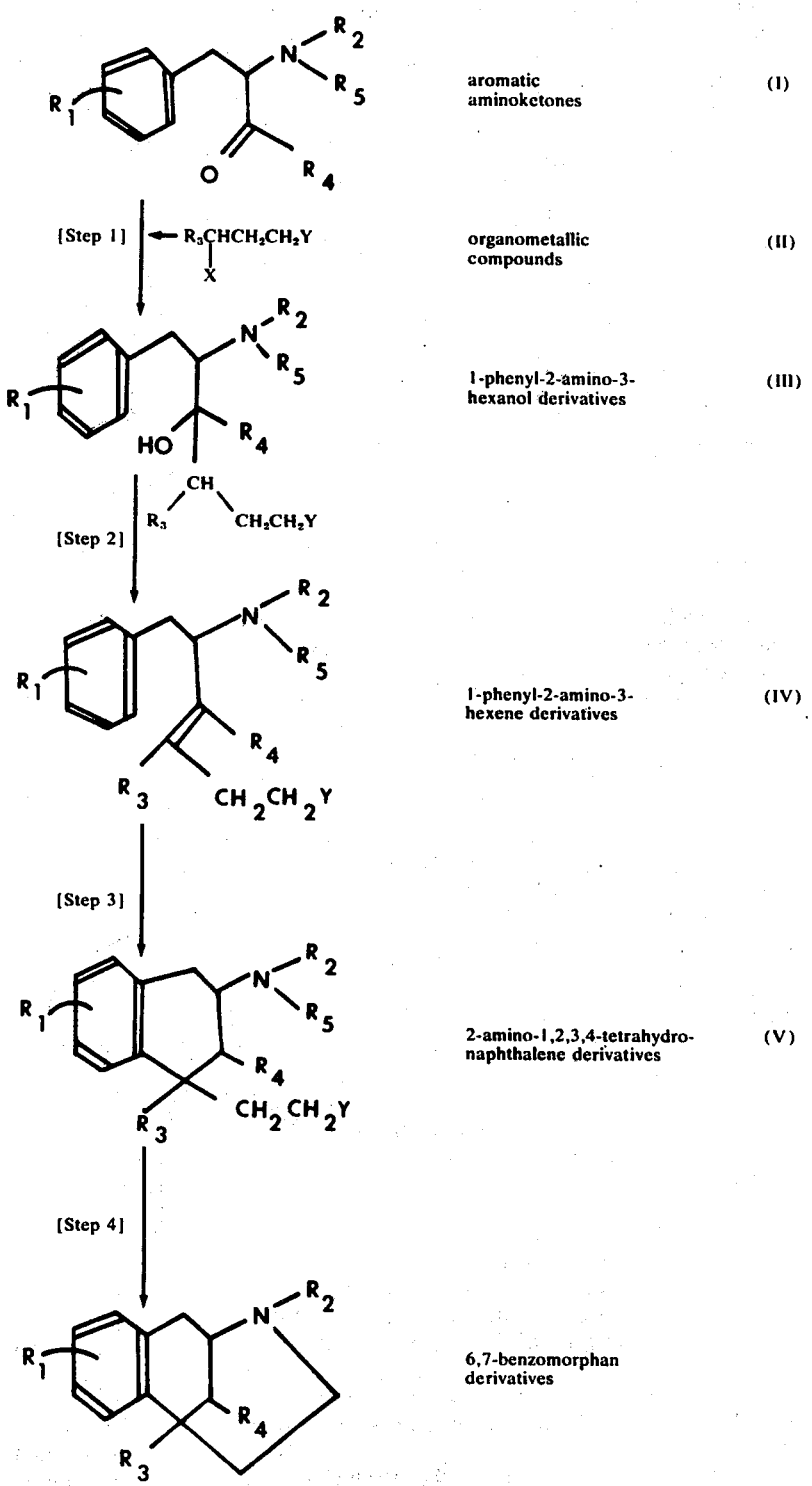

wherein $R_1$ represents a hydrogen atom, a hydroxyl group, alkyl group preferably having 1 to 4 carbon atoms, such as methyl, ethyl, isopropyl or n-butyl group, alkoxy group preferably having 1 to 4 carbon atoms, such as a methoxy, ethoxy, isopropoxy or n-butoxy group, benzyloxy group or acyloxy group preferably having 1 to 4 carbon atoms, such as a formyloxy, acetoxy, n-propionyloxy or isobutyryloxy group; $R_2$ represents a hydrogen atom, an alkyl group preferably having 1 to 8 carbon atoms, such as a methyl, ethyl, n-propyl, isobutyl, n-amyl, n-hexyl, n-heptyl or n-octyl group, substituted alkyl group (alkyl group preferably having 1 to 8 carbon atoms), the substituent being a phenyl group (for example, a benzyl or phenethyl group), benzoyl group,

group, =O group (for example, a 3-methylcarbonylpropyl group) or

group (for example, a

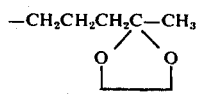

group), cycloalkyl group preferably having 3 to 6 carbon atoms, such as a cyclopropyl, cyclobutyl, cyclopentyl or cyclohexyl group, cycloalkylalkyl group preferably having 4 to 8 carbon atoms, such as a cyclopropylmethyl, cyclobutylethyl, cyclopentylmethyl, cyclohexylmethyl or 3-cyclohexylpropyl group, alkenyl group preferably having 3 to 8 carbon atoms, such as an allyl, 2-methyl-2-propenyl, 2-butenyl, 3-methyl-2-butenyl or 3-methyl-3-butenyl group or substituted alkenyl group (alkenyl group preferably having 3 to 8 carbon atoms), the substituent being a halogene atom (for example, a 3-chloro-2-propenyl, 3-bromo-2-propenyl or 2,3-dichloro-2-propenyl group; $R_3$ and $R_4$ may be the same or different and represent alkyl groups preferably having 1 to 4 carbon atoms, such as methyl, ethyl, n-propyl or isopropyl groups; $R_5$ represents a hydrogen atom or benzyl group; X represents a lithium atom or Mg-halogene groups, such as Mg-Br or Mg-Cl; and Y represents an alkoxy group preferably having 1 to 4 carbon atoms, such as a methoxy, ethoxy, isopropoxy or n-butoxy group, phenoxy group or benzyloxy group, $R_1$ and $R_2$ may be groups which are convertible to any of the corresponding substituents defined above during the reactions of the steps 1-4.

As is apparent from the above, the process of the present invention comprises four steps of reactions. Now, each of the steps is described in detail below.

[Step 1]: The reaction of the step 1 is an addition of an alkoxy-, phenoxy- or benzyloxy-alkyl group to an aromatic aminoketone of the formula (I) to produce a 1-phenyl-2-amino-3-hexanol derivative of the formula (III).

The aromatic aminoketone of the formula (I), the starting material of the present process, is prepared by a method known to the art. For example, the aromatic aminoketone of the formula (I) is prepared from phenylalanine or its derivative. Phenylalanine or its derivative is reacted with a carboxylic anhydride and successively the resultant N-acylaminoketone is hydrolyzed into an aminoketone. The reaction is known as Dakin-West reaction.

The aromatic aminoketones of the formula (I) having substituent at the amino group are prepared by ketalizing the aromatic aminoketones obtained above, introducing a suitable substituent to the amino group of the resultant aminoketals and then eliminating the ketal group by conventional means.

For example, an aromatic aminoketone is refluxed for 10 to 20 hours with heating in benzene together with 1 to 1.2 mols of ethylene glycol per 1 mol of the aminoketone in the presence of p-toluene sulfonic acid. The thus obtained aminoketal is refluxed for several hours in a solvent, for example, acetone, methanol or ethanol together with an equimol to 3 mols of a halide of a group to be introduced per 1 mol of aminoketal in the presence or absence of up to 5 mols of potassium carbonate or sodium carbonate per 1 mol of the aminoketal. The resultant product is dissolved in 5 to 10 volumes by weight of ethanol and refluxed for 1 to 20 hours with heating together with 2 to 10 mols of concentrated hydrochloric acid per 1 mol of the product. After the reflux, a substituted aminoketone can be obtained in the form of hydrochloride by removing the solvent by distillation.

The substituted or unsubstituted aromatic aminoketones of the formuls (I) may also be prepared by reacting haloketones represented by the formula

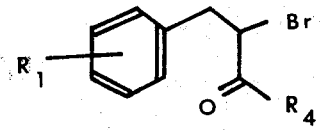

wherein $R_1$ and $R_4$ have the same significance as defined above, which are reported in Rec. Trav. Chim. 64, 129 (1945), with amines represented by the formula

wherein $R_2$ and $R_5$ have the same significance as defined above.

For example, the haloketone is dissolved in acetone or ethyl acetate and refluxed for several hours with heating together with 1 to 5 mols of the amine per 1 mol of the haloketone. The compound (I) may be obtained in the form of hydrobromide by removing the solvent by distillation.

Some of the compounds of the formula (I) have been reported in Rec. Trav. Chim., 64, 129 (1945).

As later described in detail, the amino groups of the compound (I) is desired to be completely protected in the step 3 where a naphthalene ring is formed. However, since $R_5$ is a group to be removed finally for the preparation of the desired 6,7-benzomorphan derivatives, it is favorably a group which can be so easily removed, such as a benzyl group.

The addition of the step 1 is carried out by reacting the compound (I) with an organometallic compound (II). In carrying out the reaction, the compound (I) or its solution in an inert solvent is added to an inert solvent solution containing an organometallic compound (II), such as a Grignard's reagent, at a temperature of 0°C to 40°C. The mixture is stirred at 0°C to 80°C for half an hour to 5 hours.

The organometallic compounds of the formula (II) are prepared from halides. The halides are readily prepared from the corresponding secondary alcohols through the conventional means using bromine, phosphorous tribromide, thionyl chloride, etc as a halogenating agent. The preparation of the Grignard's reagent or the lithium compound is well known to the art.

The inert solvent may be ethers, such as ethyl ether and tetrahydrofuran, aromatic hydrocarbons, such as benzene, toluene and xylene and a mixture thereof.

It is preferable to employ 1 to 5 mols of the organometallic compound per one mol of the compound (I).

After the reaction, water or an aqueous solution of ammonium chloride is added with cooling to the reaction mixture for hydrolysis. The organic solvent layer containing the resultant product of the formula (III), 1-phenyl-2-amino-3-hexanol derivatives, is dried with sodium sulfate and the solvent is removed by distillation to recover the product.

When an acid is employed for hydrolysis, the resultant product of the formula (III) may be further dehydrated to produce the compound of the formula (IV).

Where the compound (III) of high purity is required, the product is purified by silica gel chromatography. Alternatively, highly purified crystals of the compound (III) may be obtained in the form of an acid addition salt by reacting the free base form of the compound with an inorganic acid, such as hydrochloric acid or sulfuric acid or organic acid, such as oxalic acid, tartaric acid or citric acid.

Some of the new 1-phenyl-2-amino-3-hexanol derivatives have an activity of female sex hormon.

[Step 2]: In this step, 1-phenyl-2-amino-3-hexanol derivatives of the formula (III) is dehydrated into 1-phenyl-2-amino-3-hexene derivatives of the formula (IV). The reaction is carried out at 0°C to 200°C for one minute to 20 hours in the presence of a dehydrating agent. In this reaction, the compound (III) may be employed in the free base form or in the form of an acid addition salt.

The reaction may be carried out either in the presence or absence of an inert solvent. Suitable solvents are water and acetic acid.

As the dehydrating agent, mineral acids, such as sulfuric acid, phosphoric acid, hydrochloric acid, hydrobromic acid and polyphosphoric acid may be mentioned. Preferably, more than 5 mols of the dehydrating agent is employed per one mol of the compound (III).

During the dehydration reaction of the step 2, the cyclization of the compound (IV) may occur simultaneously and 2-amino-1,2,3,4-tetrahydronaphthalene derivatives of the formula (V) may be produced. Also, where the compound (III) has an alkoxy group and the like in the molecule, a hydrolysis may occur at the same time. These side reactions take place depending upon the kinds of dehydrating agents to be employed or the reaction conditions. Such side reactions may be inhibited by carrying out the dehydration reaction at a temperature below 10°C for 1 to 60 minutes using concentrated sulfuric acid as a dehydrating agent.

After the dehydration reaction, the reaction mixture is neutralized with an aqueous ammonia or sodium hydroxide and extracted with chloroform, ether or the like. After removing the solvent by distillation, the compound (IV) is obtained as an oily matter or in a semicrystalline form. Where it is necessary, the compound (IV) of a higher purity can be obtained by silica gel chromatography or crystallization into an acid addition salt, such as the hydrochloride, sulfate, oxalate, tartarate or citrate.

[Step 3]: 1-phenyl-2-amino-3-hexene derivatives of the formula (IV) obtained in the step 2 is subjected to ring closure to produce 2-amino-1,2,3,4-tetrahydronaphthlene derivatives of the formula (V). The reaction is carried out in the presence of a condensing agent at a temperature ranging from 0°C to 50°C for several minutes to 5 hours. An inert solvent such as water, acetic acid, n-hexane, preferably, carbon disulfide may be employed.

As the condensing agent, those usually used for the intramolecular ring closure of an aromatic nucleus and an olefin, for example, strong acids, such as sulfuric acid, polyphosphoric acid and hydrobromic acid Lewis acids, such as aluminum bromide and aluminum chloride may be mentioned. The use of aluminum bromide is especially preferable. Where the condensing agent is an aluminum halide, the use of 1 to 5 mols of the condensing agent per 1 mol of the compound (IV) is preferable. Where the condensing agent is other than these Lewis acids, more than 5 mols of the condensing agent per 1 mol of the compound (IV) is preferably employed.

After the completion of the reaction, the desired 2-amino-1,2,3,4-tetrahydronaphthalene derivatives are isolated, for example, by neutralizing the reaction mixture with aqueous ammonia or caustic soda, extracting the resultant solution with an appropriate solvent, for example, chloroform, ethyl ether, etc. and distilling off the solvent. Further, the desired compound can be purified, for example, by silica gel chromatography or conversion to an acid addition salt, such as the hydrochloride, oxalate or the like, followed by recrystallization.

It has been found that when the amino group of the compound (IV) is unsubstituted or mono-substituted, i.e., when the group contains at least one hydrogen atom, a cyclization to form a pyridine nucleus occurs dominantly under the reaction conditions of this step. In order to selectively produce the compound (V), the amino group of the compound (IV) is necessarily disubstituted.

[Step 4]: 2-amino-1,2,3,4-tetrahydronaphthalene derivatives of the formula (V) obtained in the step 3 are cyclized into 6,7-benzomorphan derivatives. The cyclization is achieved by reacting the compound (V) with a hydrohalogenic acid or Lewis acid in an inert solvent, or, in order to result a better yield, further reacted with an acid absorbent.

As may be understood from the above explanation in the step 3, the compounds (V) having two substituents at the amino group are practically prepared. The cyclization per se is effected regardless that the amino group of the compound (V) is completely substituted or not. However, it should be noted that when the amino group is completely substituted, the product is in the form of quaternary ammonium salt represented by the formula

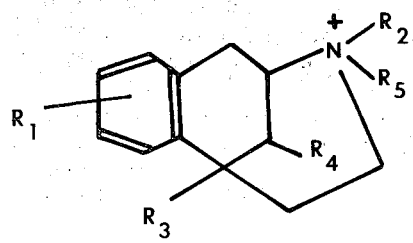

wherein $R_1 - R_5$ have the same significance as defined above but $R_2$ and $R_5$ are not hydrogen atoms. Therefore, the product is subjected to a hydrogenolysis to result the final product of 6,7-benzomorphan derivative.

On the other hand, when the amino group of the compounds (V) has at least one hydrogen atom, the cyclization reaction results a direct production of 6,7-benzomorphan derivatives.

Thus, a hydrogenolysis procedure is practically required before or after the cyclization reaction of the step 4 to obtain the desired 6,7-benzomorphan derivatives. Such a hydrogenolysis may be carried out by a conventional method. For example, the compound (V) having a certain substituent as $R_2$ and a benzyl group as $R_5$ is dissolved in a suitable solvent and hydrogenolyzed at room temperature to 50°C under acidic conditions in a hydrogenous atmosphere using palladium-carbon or palladium black as the catalyst. After the completion of hydrogenolysis, the catalyst is separated by filtration and the filtrate is distilled to remove the solvent. The residue is neutralized and extracted with chloroform. The oily matter obtained after the distillation of chloroform is subjected to a vacuum distillation to result the corresponding compound (V) where the benzyl group is removed. The hydrogenolysis of the quaternary ammonium salt may be carried out by a same method excluding the acidic conditions.

When both of the hydrogen atoms of the amino group are protected by benzyl groups, only one of the benzyl group is eliminated by using palladium-carbon as the catalyst while both of the benzyl groups are eliminated at the same time by using palladium black.

In carrying out the cyclization of the compound (V), where the compound (V) is reacted with a hydrohalogenic acid, such as hydrobromic acid or hydroiodic acid, the reaction is carried out in an inert solvent, preferably, water, acetic acid or their mixture at a temperature ranging from 50° to 150°C for several minutes to several hours. Preferably, an equimolar amount to a large excess of the hydrohalogenic acid is employed based on the amount of the compound (V).

Where the compound (V) is reacted with a Lewis acid, such as aluminum tribromide, aluminum chloride or boron tribromide, the reaction is carried out in an inert solvent at a temperature ranging from −70°C up to the boiling point of the solvent for 2 minutes to several hours. As the inert solvent, chlorinated aliphatic hydrocarbons, such as ethane dichloride and dichloroethane, and aliphatic saturated hydrocarbons, such as carbon disulfide and n-hexane are preferable. Preferably, 1 mol to 10 mols of the Lewis acid is employed per 1 mol of the compound (V).

After the reaction, the reaction mixture is neutralized with an alkali and extracted with a suitable solvent such as chloroform, dichloromethane, ethylether, dioxane, tetrahydrofuran, etc. The solvent is removed by distillation from the extract to give a residue containing 6,7-benzomorphan derivatives. The cyclization of the compound (V) into 6,7-benzomorphan derivative is not always complete upon the reaction with hydrohalogenic acid or Lewis acid. A better yield is achieved by further reacting the above obtained residue with an acid absorbent.

For example, the residue is dissolved in an inert solvent and heated together with an acid absorbent at a temperature of 50° to 60°C for several minutes to several hours. As the suitable solvent, alkanons, such as acetone and methyl ethyl ketone and alkanol, such as ethanol and methanol may be mentioned.

As the acid absorbent, either inorganic or organic basic substances including alkali metal carbonate, such as sodium carbonate and potassium carbonate, alkali metal bicarbonate, such as sodium bicarbonate and potassium bicarbonate, hydroxides of alkali metals or alkaline earth metals, such as sodium hydroxide, potassium hydroxide and barium hydroxide, ammonia, alkali metal acetate, such as sodium acetate, alkali metal propionate, such as sodium propionate and tertiary amines, such as triethylamine, trimethylamine and N,N-dimethyl aniline may be used. Especially preferred are sodium or potassium bicarbonate.

The amount of the acid absorbent to be employed may be an equimol to a large excess based on the amount of the starting compounds, 2-amino-1,2,3,4-tetrahydronaphthalene derivatives.

After the reaction, the reaction mixture is subjected to filtration and the filtrate is concentrated to give crude 6,7-benzomorphan derivatives.

When the 6,7-benzomorphan derivatives are obtained in the form of quaternary ammonium salt, the products are subjected to the hydrolysis as mentioned above.

The crude 6,7-benzomorphan derivatives may be purified by a silica gel chromatography or by crystallization as an acid addition salt such as the hydrochloride, sulfate, hydrobromide, citrate or oxalate. Further, purified 6,7-benzomorphan derivatives are obtained in the form of methiodide.

As is already described in the step 3, when the amino group of the compound (IV) has at least one hydrogen atom, a cyclization to form a pyridine nucleus occurs rather dominantly under the reaction conditions of the step 3. The product is a 2-benzyl-1,2,5,6-tetrahydropyridine derivative represented by the formula

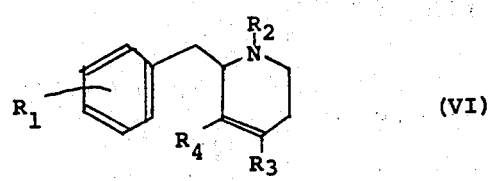

wherein $R_1$, $R_2$, $R_3$ and $R_4$ have the same significance as defined above.

This product is known to be an intermediate for the preparation of 6,7-benzomorphan derivative according to the prior art process. The cyclization of the compound (IV) into the compound (VI) may be almost selectively conducted under the specific conditions.

For example, 1-phenyl-2-amino-3-hexene derivatives (IV) are reacted in an inert solvent with boron tribromide or boron trichloride at a temperature ranging from −70° to 100°C for half an hour to 20 hours. As the solvent, aromatic hydrocarbons, such as benzene, toluene and xylene and halogenated aliphatic hydrocarbons, such as chloroform, dichloromethane and dichloroethane may be used. Preferably, 1 mol to 5 mols of boron trichloride or boron tribromide may be employed.

After the reaction, the reaction mixture is neutralized with an aqueous ammonia or aqueous sodium hydroxide and the layer of the organic solvent is separated. After distilling off the solvent, the compound (VI) is obtained as an oily matter.

The thus obtained compound (VI) can be purified in the free form by distillation. Alternatively, the compound (VI) can be purified by crystallization into an acid addition salt, for example, an inorganic acid salt, such as the hydrochloride, hydrobromide or sulfate or an organic acid salt, such as the citrate, oxalate or tartrate.

Now, the present invention is further illustrated by the following examples.

EXAMPLE 1

1-phenyl-2-(N-benzyl)amino-3-hydroxy-3,4-dimethyl-6-ethoxyhexane

A Grignard's reagent is prepared from 9.0 g of Mg, 69 g of 4-ethoxy-2-butyl bromide and 200 ml of ethyl ether. A solution of 14 g of α-(N-benzyl)amino-α-benzylacetone in 100 ml of benzene is added dropwise to the Grignard's reagent. After the addition, the mixture is stirred at 20° to 30°C for 3 hours and then cooled with ice. To the resultant mixture is added 100 ml of water. The layer of the organic solvent is separated by decantation, washed with water and dried with sodium sulfate. The solvent is removed by distillation. The residue is dissolved in 100 ml of ethyl ether. To the solution is added a solution of oxalic acid in acetone so that the pH is adjusted to 3.0 to 5.5. The unreacted raw materials and a small amount of impurities are crystalized as oxalates. The crystals are removed by filtration. The filtrate is concentrated. The concentrate is neutralized by the addition of an aqueous ammonia and then extracted with ethyl ether. The ether layer is washed with water and dried with sodium sulfate. The solvent is removed by distillation. As the result, 10 g of 1-phenyl-2-(N-benzyl)amino-3-hydroxy-3,4-dimethyl-6-ethoxyhexane is obtained as a yellow, oily matter. Infrared absorption spectrum $\lambda_{max}^{liquid\ film}$: 3400 (broad), 2950, 2930, 2870, 1603, 1496, 1110 (broad), 740, 700

Elementary analysis, Calculated for $C_{23}H_{33}NO_2$: C, 77.70%; H, 9.36%; N, 3.94% Found: C, 78.01%, H, 9.13%; N, 3.58%.

EXAMPLE 2

1-phenyl-2-(N-methyl-N-benzyl)amino-3-hydroxy-3,4-dimethyl-6-ethoxyhexane oxalate A Grignard's reagent is prepared from 6.0 g of Mg, 45.5 g of 4-ethoxy-2-butyl bromide, and 200 ml of ethyl ether. A solution of 7.0 g of α-(N-methyl-N-benzyl)amino-α-benzylacetone in 100 ml of tetrahydrofuran is added to the Grignard's reagent and the mixture is stirred at room temperature for one and a half hours. The reaction mixture is cooled with ice. 30 ml of water is added to the mixture. The layer of the organic solvent is separated by decantation, washed with water and dried with sodium sulfate. The solvent is removed by distillation. The residue is dissolved in acetone and a solution of 2.5 g of oxalic acid in 20 ml of acetone is added to the solution. The solvent is removed by distillation and the resultant solids are recrystallized from isopropanol-ethyl ether. As the result, 7.3 g of oxalate of 1-phenyl-2-(N-methly-N-benzyl) amino-3-hydroxy-3,4-dimethyl-6-ethoxyhexane is obtained.

Melting point: 122° – 124°C, Elementary analysis, Calculated for $C_{26}H_{37}NO_6$: C, 67.95%; H, 8.12%; N, 3.05%, Found: C, 67.92%; H, 8.41%; N, 2.97%.

EXAMPLE 3

1-(p-methoxy)phenyl-2-(N-benzyl)amino-3-hydrxy-3,4-dimethyl-6-ethoxyhexane

The procedure described in Example 1 is repeated except that 13.0 g of α-(N-benzyl)amino-α-(p-methoxy)benzylacetone is used as the starting compound aminoketone. As the result, 9.2 g of 1-(p-methoxy)phenyl-2-(N-benzyl)amino-3-hydroxy-3,4-dimethyl-6-ethoxyhexane is obtained as a yellow, oily matter.

Elementary analysis, Calculated for $C_{24}H_{35}NO_3$: C, 74.77%; H, 9.15%; N, 3.63%, Found: C, 74.29% H, 9.19%; N, 3.85%, Infrared absorption spectrum $\lambda_{max}^{liquid\ film}$: 3400 (broad), OH, C>O not observed.

EXAMPLE 4

1-(p-methoxy)phenyl-2-amino-3-hydroxy-3,4-dimethyl-6-ethoxyhexane

A Grignard's reagent is prepared from 5.8 g of Mg, 43.5 g of 4-ethoxy-2-butyl bromide and 150 ml of ethyl ehter. 100 ml of tetrahydrofuran is added to the Grignard's reagent and the mixture is cooled to 10° to 20°C. 4.6 g of α-amino-α-(p-methoxy)benzylacetone hydrochloride is added to the mixture little by litted in several divisions. The mixture is stirred for one hour and then cooled with ice. 50 ml of water is added to the resultant mixture. The layer of the organic solvent is separated by decantation, washed with water and dried with sodium sulfate. The solvent is removed by distillation. The resultant oily matter is subjected to distillation. As the result, 3 g of 1-(p-methoxy)phenyl-2-amino-3-hydroxy-3,4-dimethyl-6-ethoxyhexane is obtained as fractions having a boiling point of 185° to 190°C/1 mm Hg.

Infrared absorption spectrum $\lambda_{max}^{liquid\ film}(cm^{-1})$: 3400 (broad), 2960, 2930, 2870, 1607, 1580, 1507, 1105, NMR spectrum:

$\delta_{TMS}^{CDCl_3}$ 1.10 (3H, sinlet, $-\overset{|}{\underset{|}{C}}-CH_3$)ppm $\delta_{TMS}^{CDCl_3}$ 0.85 – 1.30 (6H, multiplet, $CH_3-CH-CH_2$)ppm
$\delta_{TMS}^{CDCl_3}$ 3.80 (3H, singlet, $OCH_3$)ppm
$\delta_{TMS}^{CDCl_3}$ 6.75 – 7.20 (4H, quadruplet, para-substituted aromatic ring proton)ppm

EXAMPLE 5

1-phenyl-2-(N-benzyl)amino-3-hydroxy-3,4-dimethyl-6-methoxyhexane

The procedure described in Example 1 is repeated except that 65 g of 4-methoxy-2-butyl bromide is used in place of 4-ethoxy-2-butyl bromide. As the result, 12.0 g of 1-phenyl-2-(N-benzyl)amino-3-hydroxy-3,4-dimethyl-6-methoxyhexane is obtained as a yellow, oily matter.

Elementary analysis, Calculated for $C_{22}H_{31}NO_2$: C, 77.38%; H, 9.15%; N, 4.10%, Found: C, 77.08%; H, 8.79%; N, 4.07%.

EXAMPLE 6

1-phenyl-2-(N-methyl-N-benzyl)amino-3-hydroxy-3,4-dimethyl-6-methoxyhexane

The procedure described in Example 1 is repeated except that 7.0 g of α-(N-methyl-N-benzyl)amino-α-benzyl-acetone is used in place of α-(N-benzyl)amino-α-benzyl-acetone and 40.0 g of 4-methoxy-2-butyl bromide is used in place of 4-ethoxy-2-butyl bromide and 6.0 g of Mg is used. As the result, 6.8 g of 1-phenyl-2-(N-methyl-N-benzyl)amino-3-hydroxy-3,4-dimethyl-6- methoxyhexane is obtained as a yellow, oily matter.

Elementary analysis Calculated for $C_{22}H_{33}NO_2$: C, 77.70%; H, 9.36%; N, 3.94%
Found: C, 78.04%; H, 9.31%; N, 3.72%

EXAMPLE 7

1-(p-methoxy)phenyl-2-(N-benzyl)amino-3-hydroxy-3,4-dimethyl-6-methoxyhexane

The procedure described in Example 1 is repeated except that 65 g of 4-methoxy-2-butyl bromide is used in place of 4-ethoxy-2-butyl bromide and 13.0 g of α-(N-benzyl)amino-α-p-methoxybenzylacetone is used in place of α-(N-benzyl)amino-α-benzylacetone. As the result, 8.9 g of 1-(p-methoxy)phenyl-2-(N-benzyl)amino-3-hydroxy-3,4-dimethyl-6-methoxyhexane is obtained as a yellow, oily matter.

Infrared absorption spectrum $\lambda_{max}^{liquid\ film}(cm^{-1})$: 3450 (OH), 1607, 1594 (benzene nucleus), 1509 (benzene nucleus), 1105 (ethyl ether).

Elementary analysis, Calculated for $C_{23}H_{33}NO_3$: C, 74.36%; H, 8.95%; N, 3.77%, Found: C, 74.85%; H, 8.77%; N, 3.69%.

EXAMPLE 8

1-(p-methoxy)phenyl-2-(N,N-dibenzyl)amino-3-hydroxy-3,4-dimethyl-6-methoxyhexane The procedure described in Example 1 is repeated except that 65 g of 4-methoxy-2-butyl bromide is used in place of 4-ethoxy-2-butyl bromide and 10.0 g of α-(N,N-dibenzyl)amino-α-(p-methoxy)benzylacetone is used in place of α-(N-benzyl)amino-α-benzylacetone. As the result, 9.2 g of 1-(p-methoxy)phenyl-2-(N,N-dibenzyl)amino-3-hydroxy-3,4-dimethyl-6-methoxyhexane is obtained as a yellow, oily matter.

Elementary analysis Calculated for $C_{30}H_{39}NO_3$: C, 78.05%; H, 11.74%; N, 3.03% Found: C, 78.31%; H, 11.88%; N, 2.92%

EXAMPLE 9

1-(p-methoxy)phenyl-2-(N-methyl-N-benzyl)amino-3-hydroxy-3,4-dimethyl-6-ethoxyhexane oxalate The procedure described in Example 2 is repeated except that 6.5 g of α-(N-methyl-N-benzyl)amino-α-(p-methoxy)benzylacetone is used as the starting material in place of α-(N-methyl-N-benzyl)amino-α-benzylacetone. As the result, 8.0 g of oxalate of 1-p-methoxyphenyl-2-(N-methyl-N-benzyl)amino-3-hydroxy-3,4-dimethyl-6-ethoxyhexane is obtained.

Melting point: 105° – 107°C Elementary analysis, Calculated for $C_{27}H_{39}NO_7$: C, 66.23%; H, 8.03%; N, 2.86%, Found: C, 66.35%; H, 8.01%; N, 2.66%.

EXAMPLE 10

1-(p-methoxy)phenyl-2-(N-methyl-N-benzyl)amino-3-hydroxy-3,4-dimethyl-6-methoxyhexane oxalate The procedure described in Example 2 is repeated except that 6.5 g of α-(N-methyl-N-benzyl)amino-α-p-methoxy-benzylacetone is used in place of α-(N-methyl-N-benzyl)amino-α-benzylacetone and 40.0 g of 4-methoxy-2-butyl bromide is used in place of 4-ethoxy-2-butyl bromide. As the result, 7.3 g of oxalate of 1-p-methoxyphenyl-2-(N-methyl-N-benzyl)amino-3-hydroxy-3,4-dimethyl-6-methoxyhexane is obtained.

Melting point: 125° – 127°C.

Elementary analysis, Calculated for $C_{26}H_{37}NO_7$: C, 65.66%; H, 7.84%; N, 2.95%, Found: C, 65.43%; H, 7.90%; N, 3.02%.

EXAMPLE 11

1-(p-methoxy)phenyl-2-(N-benzyl)amino-3,4-dimethyl-6-methoxy-3-hexene 10 g of 1-(p-methoxy)phenyl-2-(N-benzyl)amino-3-hydroxy-3,4-dimethyl-6-methoxyhexane obtained according to the procedure described in Example 7 is added dropwise to 100 ml of 93% sulfuric acid cooled to a temperature of −5% to 5°C with stirring. The addition is complete in half an hour. The stirring is continued for further 10 minutes at the same temperature. The mixture is neutralized with an ice-cooled aqueous ammonia and extracted with ethyl ether. The ether layer is washed with water and dried with sodium sulfate. The solvent is removed by distillation. After distillation of the residue, 4 g of 1-(p-methoxy)phenyl-2-(N-benzyl)amino-3,4-dimethyl-6-methoxy-3-hexene is obtained as fractions having a boiling point of 205° – 210°C/1 mm Hg.

Elementary analysis, Calculated for $C_{23}H_{31}NO_2$: C, 78.15%; H, 8.84%; N, 3.96%, Found: C, 77.89%; H, 8.60%; N, 4.10%.

EXAMPLE 12

1-phenyl-2-(N-benzyl)amino-3,4-dimethyl-6-methoxy-3-hexene

The procedure described in Example 11 is repeated except that 10 g of 1-phenyl-2-(N-benzyl)amino-3-hydroxy-3,4-dimethyl-6-methoxyhexane obtained according to the procedure described in Example 5 is used in place of 1-(p-methoxy)phenyl-2-(N-benzyl)amino-3-hydroxy-3,4-dimethyl-6-methoxyhexane and 95% sulfuric acid is used in place of 93% sulfuric acid. As the result, 6 g of 1-phenyl-2-(N-benzyl)amino-3,4-dimethyl-6-methoxy-3-hexene is obtained as fractions having a boiling point of 191° – 196°C/1 mm Hg.

Elementary analysis, Calculated for $C_{22}H_{29}NO$: C, 81.69%; H, 9.04%; N, 4.33%, Found: C, 81.73%; H, 9.11%; N, 4.22%.

EXAMPLE 13

1-phenyl-2-(N-benzyl)amino-3,4-dimenthyl-6-ethoxy-3-hexene

The procedure described in Example 11 is repeated except that 10 g of 1-phenyl-2-(N-benzyl)amino-3-hydroxy-3,4-dimethyl-6-ethoxyhexane obtained according to the procedure described in Example 1 is used in place of 1-(p-methoxy)phenyl-2-(N-benzyl)amino-3-hydroxy-3,4-dimethyl-6-methoxyhexane. As the result, 5.8 g of 1-phenyl-2-(N-benzyl)amino-3,4-dimethly-6-ethoxy-3-hexene is obtained as fractions having a boiling point of 194° – 201°C/1 mm Hg.

Elementary analysis, Calculated for $C_{23}H_{31}NO$: C, 82.77%; H, 92.6%; N, 4.15%, Found: C, 82.87%; H, 9.19%; N, 4.10%.

EXAMPLE 14

1-(p-methoxy)phenyl-2-(N-benzyl)amino-3,4-dimethyl-6-ethoxy-3-hexene

The procedure described in Example 11 is repeated except that 10 g of 1-(p-methoxy)phenyl-2-(N-benzyl)amino- 3-hydroxy-3,4-dimethyl-6-ethoxyhexane obtained according to the procedure described in Example 3 is used in place of 1-(p-methoxy)phenyl-2-(N-benzyl)amino-3-hydroxy-3,4-dimethyl-6-methoxyhexane. As the result, 3.5 g of 1-(p-methoxy)phenyl-2-(N-benzyl)amino-3,4-dimethyl-6-ethoxy-3-hexene is obtained as fractions having a boiling point of 208° – 214°C/1 mm Hg.

Elementary analysis, Calculated for $C_{24}H_{33}NO_2$: C, 78.43%; H, 9.05%; N, 3.81%, Found: C, 78.39%; H, 9.06%; N, 3.83%.

EXAMPLE 15

1-phenyl-2-(N-methyl-N-benzyl)amino-3,4-dimethyl-6-ethoxy-3-hexene 10 g of 1-phenyl-2-(N-methyl-N-benzyl)amino-3-hydroxy-3,4-dimethyl-6-ethoxyhexane oxalate obtained according to the procedure described in Example 2 is added to 98% sulfuric acid at 0° – 10°C with stirring. The mixture is neutralized with an aqueous ammonia and extracted with ethyl ether. The ether extract is subjected to distillation. 6.0 g of 1-phenyl-2-(N-methyl-N-benzyl)amino-3,4-dimethyl-6-ethoxy-3-hexene is obtained as fractions having a boiling point of 163°– 167°C/0.6 mm Hg. Infrared absorption spectrum (liquid film): OH not observed.

NMR spectrum:

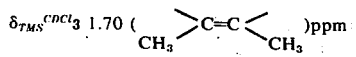

$\delta_{TMS}^{CDCl_3}$ 1.70 ( CH$_3$>C=C<CH$_3$ )ppm

EXAMPLE 16

1-phenyl-2-(N-methyl-N-benzyl)amino-3,4-dimethyl-6-methoxy-3-hexene 1-phenyl-2-(N-methyl-N-benzyl)amino-3-hydroxy-3,4dimethyl-6-methoxyhexane obtained according to the procedure described in Example 6 is converted to the oxalate according to the procedure described in Example 2.

The procedure described in Example 15 is repeated except that 10 g of the thus obtained 1-phenyl-2-(N-methly-N-benzyl)amino-3-hydroxy-3,4-dimethyl-6-methoxyhexane oxalate is used in place of 1-phenyl-2-(N-methyl-N-benzyl)amino-3-hydroxy-3,4-dimethyl-6-ethoxyhexane oxalate. As the result, 5.3 g of 1-phenyl-2-(N-methyl-N-benzyl)amino-3,4-dimethyl-6-methoxy-3-hexene is obtained as fractions having a boiling point of 161° – 165°C/0.4 mm Hg.

EXAMPLE 17

1-(p-methoxy)phenyl-2-(N-methyl-N-benzyl)amino-3,4-dimethyl-6-ethoxy-3-hexene

The procedure described in Example 15 is repeated except that 10 g of 1-(p-methoxy)phenyl-2-(N-methyl-N-benzyl)amino-3-hydroxy-3,4-dimethyl-6-ethoxyhexane oxalate obtained according to the procedure described in Example 9 is used in place of 1-phenyl-2-(N-methyl-N-benzyl)amino-3-hydroxy-3,4-dimethyl-6-ethoxyhexane oxalate. As the result, 4.5 g of 1-(p-methoxy)phenyl-2-(N-methyl-N-benzyl)amino-3,4dimethyl-6-ethoxy-3-hexene is obtained as fractions having a boiling point of 172° – 176°C/0.6 mm Hg.

EXAMPLE 18

1-(p-methoxy(-phenyl-2-(N,N-dibenzyl)amino-3,4-dimethyl-6-methoxy-3-hexene 1-(p-methoxy)phenyl-2-(N,N-dibenzyl)amino-3-hydroxy-3,4-dimethyl-6-methoxyhexane obtained according to the procedure described in Example 8 is converted to the oxalate according to the procedure described in Example 2.

The procedure described in Example 15 is repeated except that 10 g of the thus obtained 1-(p-methoxy)-phenyl-2-(N,N-dibenzyl)amino-3-hydroxy-3,4dimethyl-3-hexene oxalate is used in place of 1-phenyl-2-(N-methyl-N-benzyl)amino-3-hydroxy-3,4-dimethyl-6-ethoxyhexane oxalate. As the result, 3.8 g of 1-(p-methoxy)phenyl-2-(N,N-dibenzyl)amino-3,4-dimethyl-6-methoxy-3-hexene is obtained as fractions having a boiling point of 215° – 225°C/0.05 mm Hg.

EXAMPLE 19

1,2,3,4-tetrahydro-2-(N-methyl)amino-3,4-dimethyl-4-(β-ethoxy)ethyl naphthalene 7 g of 1-phenyl-2-(N-methyl-N-benzyl)amino-3,4-dimethyl-6-ethoxy-3-hexene obtained according to the procedure described in Example 15 is dissolved in 100 ml of carbon disulfide. 7 g of anhydrous aluminum bromide is added to the solution. The mixture is allowed to react at 20°–30°C for one hour and than refluxed for several minutes. The solvent is removed by distillation. An aqueous ammonia is added to the residue and extraction is carried out with chloroform. The extract is subjected to distillation. 2g of 1,2,3,4-tetrahydro-2-(N-methyl-N-benzyl)amino- 3,4-dimethyl-4-(β-ethoxy)ethylnaphthalene is obtained as fractions having a boiling point of 187° – 190°C/0.3 mm Hg.

An infrared absorption spectrum (liquid film) of the product reveals absorption of mono- and ortho- substituted benzene nuclei at 695, 735 and 760 cm$^{-1}$ and an absorption of ethoxy group at 1105 cm$^{-1}$. As the result of an NMR spectrum, it is observed that the absorption of hydrogen atoms of the methyl groups bonded to the double bond is disappeared.

1.7 g of the product is dissolved in 10 ml of dioxane and the solution is acidified with hydrochloric acid. The resultant solution is subjected to hydrogenolysis at room temperature and under atmospheric pressure using 1 g of palladium-carbon as a catalyst. After the reaction, the catalyst is removed by filtration and the solvent is distilled off. The residue is neutralized with an aqueous ammonia and extracted with chloroform. The chloroform is distilled off and the resultant oily matter is subjected to distillation. 0.8 g of 1,2,3,4-tetrahydro-2-(N-methyl)amino-3,4-dimethyl-4-(β-ethoxy)ethylnaphthalene is obtained as fractions having a boiling point of 125° – 130°C/1 mm Hg. An infrared absorption spectrum of the product reveals an absorption of N–H at 3300 cm$^{-1}$.

Elementary analysis, Calculated for $C_{17}H_{27}$; NO: C, 78.11%; H, 10.41%; N, 5.36%, Found: C, 77.89%; H, 10.72%; N, 5.2%.

EXAMPLE 20

1,2,3,4-tetrahydro-2-(N-methyl)amino-3,4-dimethyl-4-(β-methoxyethylnaphthalene

The procedure described in Example 19 is repeated except that 8 g of 1-phenyl-2-(N-methyl-N-benzyl) amino-3,4-dimethyl-6-methoxy-3-hexene obtained according to the procedure described in Example 16 is used in place of 1-phenyl-2-(N-methyl-N-benzyl-)amino-3,4-dimethyl-6-ethoxy-3-hexene and 8 g of anhydrous aluminum bromide is used. As the result, 2.3 g of 1,2,3,4-tetrahydro-2-(N-methyl-N-benzyl)amino-3,4-dimethyl-4-(β-methoxy) ethylnaphthalene is obtained as fractions having a boiling point of 185° –

188°C/0.5 mm Hg.

2.3 g of the product is dissolved in 15 ml of dioxane and the solution is acidified with hydrochloric acid. The resultant solution is subjected to hydrogenolysis in the same manner as described in Example 19. 1.4 g of 1,2,3,4-tetrahydro-2-(N-methyl)amino-3,4-dimethyl-4-(β-methoxy)ethylnaphthalene is obtained as fractions having a boiling point of 122° – 126°C/1 mm Hg.

EXAMPLE 21

1,2,3,4-tetrahydro-2-(N-methyl)amino-3,4-dimethyl-4-(β-ethoxy)ethyl-6-methoxynaphthalene The procedure described in Example 19 is repeated except that 7 g of 1-(p-methoxy)phenyl-2-(N-methyl-N-benzyl)amino-3,4-dimethyl-6-ethoxy-3-hexene obtained according to the procedure described in Example 17 is used in place of 1-phenyl-2-(N-methyl-N-benzyl)amino-3,4-dimethyl-6-ethoxy-3-hexene. As the result, 0.8 g of 1,2,3,4-tetrahydro-2-(N-methyl-N-benzyl)amino-3,4-dimethyl-4-(β-ethoxy)ethyl-6-methoxynaphthalene is obtained as fractions having a boiling point of 193° – 201°C/0.3 mm Hg.

0.6 g of the product is dissolved in 10 ml of dioxane and the solution is acidified with hydrochloric acid. The resultant solution is subjected to hydrogenolysis in the same manner as described in Example 19. 0.35 g of 1,2,3,4-tetrahydro-2-(N-methyl)amino-3,4-dimethyl-4-(β-ethoxy)ethyl-6-methoxynaphthalene is obtained as fractions having a boiling point of 136° – 140°C/1 mm Hg.

EXAMPLE 22

2,5,9-trimethyl-6,7-benzomorphan methiodide 20 ml of 48% hydrobromic acid is added to 1 g of 1,2,3,4-tetrahydro-2-(N-methyl)amino-3,4-dimethyl-(β-ethoxy)ethylnaphthalene obtained according to the procedure described in Example 19 and the mixture is refluxed for 3 hours. After cooling, the mixture is neutralized with an aqueous ammonia and extracted with chloroform. The chloroform layer is washed with water and dried with sodium sulfate. The solvent is distilled off. The residue is dissolved in 20 ml of acetone. 1 g of sodium hydrogen carbonate is added to the solution and the mixture is refluxed for one hour. Insoluble matters are removed by filtration and the solvent is distilled off. 0.6 g crude 2,5,9-trimethyl-6,7-benzomorphan is obtained.

The crude product is converted to the corresponding methiodide according to the method described in J. Org. Chem., 28, 1869 (1963). Upon recrystallization from ethyl alcohol-ethyl acetate, crystals of 2,5,9-trimethyl-6,7-benzomorphan methiodide is obtained.

Melting point: 217° – 220°C (218° – 222°C as described in the above literature) Elementary analysis, Calculated for $C_{16}H_{24}NI$: C, 53.78%; H, 6.77%; N, 3.92%, Found: C, 53.71%; H, 6.54%; N, 3.79%.

EXAMPLE 23

2,5,9-trimethyl-6,7-benzomorphan methiodide

The procedure described in Example 22 is repeated except that 1 g of 1,2,3,4-tetrahydro-2-(N-methyl)amino-3,4-dimethyl-4-(β-methoxy)ethylnaphthalene obtained according to the procedure described in Example 20 is used in place of 1,2,3,4-tetrahydro(N-methyl)amino-3,4-dimetyl-4-(β-ethoxy)ethylnaphthalene. As the result, 0.4 of 2,5,9-trimethyl-6,7-benzomorphan methiodide is obtained.

Melting point: 216° – 221°C

EXAMPLE 24

2,5,9-trimethyl-2'-hydroxy-6,7-benzomorphan hydrochloride

The procedure described in Example 22 is repeated except that 1 g of 1,2,3,4-tetrahydro-2-(N-methyl)amino-3,4-dimethyl-4-(β-ethoxy)ethyl-6-methoxynaphthalene obtained according to the procedure described in Example 21 is used in place of 1,2,3,4-tetrahydro-2-(N-methyl)amino-3,4-dimethyl-4-(β-ethoxy)ethylnaphthalene. 0.4 g of the crude 2,5,9-trimethyl-2'-hydroxy-6,7-benzomorphan is obtained. The crude product is converted to the hydrochloride according to the method described in J. Org. Chem., 28, 2479 (1963). After recrystallization from methanol, the resultant crystals of 2,5,9-trimethyl-2'-hydroxy-6,7-benzomorphan hydrochloride shows a melting point of 267° – 270°C [269° – 272°C as described in J. Org. Chem., 28, 2479 (1963)]. The product corresponds well with an authentic product prepared according to the process described in the above literature in the NMR and infrared absorption spectra.

EXAMPLE 25

1-benzyl-2-(p-hydroxy)benzyl-3,4-dimethyl-1,2,5,6-tetrahydropyridine oxalate 2 g of 1-(p-methoxy)phenyl-2-(N-benzyl)amino-3,4-dimethyl-6-methoxy-3-hexene obtained according to the procedure described in Example 11 is dissolved in 10 ml of dichloromethane. The solution is added to a solution of 6 g of boron tribomide in 15 ml of dichloromethane at −70° to −50°C. The mixture is stirred at the same temperature for half an hour to two hours. Then, the temperature of the mixture is gradually elevated to room temperature and the solvent is removed by vacuum distillation.

To the residue is added an ice-cooled aqueous ammonia. Extraction is carried out with chloroform. The chloroform layer is washed with water, dried and concentrated. The concentrate is passed through a column of 200 ml silica gel G. Elution is carried out with a mixture of 10 parts of dioxane and one part of ethyl ether. The eluate is concentrated and, as the result, 0.4 g of 1-benzyl-2-(p-hydroxy)benzyl-3,4-dimethyl-1,2,5,6-tetrahydro-pyridine is obtained.

A thin layer chromatography of the compound thus obtained using a solvent system of chloroform, methanol and acetic acid (8:1:4) and a color reagent of iodine reveals an Rf value of 0.80. Further, the compound is subjected to a gas chromatography under the following conditions.

Apparatus: Shimadzu GC-5ATC (product of Shimadzu Seisakusho Ltd., Japan), Column liquid: Silicone SE 52.

Column size: 3 mmφ × 1.5 m
Column temperature: 250°C
Carrier gas: nitrogen, 40 ml/min.

The retention time obtained as the result of the gas chromatography is identical with that of the authentic compound prepared from 1-benzyl-2-(p-methoxy)benzyl-3,4-dimethyl-1,2,5,6-tetrahydropyridine [prepared according to the method described in J. Med. Chem., 13, 302 (1970)] and 48% hydrobromic acid according to the method described in J. Org. Chem., 28, 2470 (1963).

The free amine of 1-benzyl-2-(p-hydroxy)benzyl-3,4-dimethyl-1,2,5,6-tetrahydropyridine is dissolved in acetone. Oxalic acid is added to the resultant solution. As the result, the oxalate of the compound is obtained.

Melting poing: 123° –125°C Elementary analysis, Calculated for $C_{23}H_{27}NO_5$: C, 69.50%; H, 6.85%; N, 3.52%, Found: C, 69.91%; H, 6.77%; N, 3.61%.

EXAMPLE 26

1,2-dibenzyl-3,4-dimethyl-1,2,5,6-tetrahydropyridine oxalate

The procedure described in Example 25 is repeated except that 1-phenyl-2-(N-benzyl)amino-3,4-dimethyl-6-methoxy-3-hexene obtained according to the procedure described in Example 12 is used in place of 1-(p-methoxy)phenyl-2-(N-benzyl)amino-3,4-dimethyl-6-methoxy-3-hexene. As the result, the oxalate of 1,2-dibenzyl-3,4-dimethyl-1,2,5,6-tetrahydropyridine is obtained.

Melting point: 178°– 180°C Elementary analysis, Calculated for $C_{23}H_{27}NO_4$: C, 72.42%; H, 7.13%; N, 3.67%, Found: C, 71.99%; H, 7.07%; N, 3.92%, NMR spectrum (free amine).

$\delta_{TMS}^{CDCl_3}$ 1.60 (6H, singlet, $H_3C\!\!>\!\!C=C\!\!<\!\!CH_3$ )ppm $\delta_{TMS}^{CDCl_3}$ 3.54 (2H, singlet, N—CH$_2$—⌬ )ppm $\delta_{TMS}^{CDCl_3}$ 7.00, 7.10 (10H, singlet, respectively; aromatic nucleus hydrogen)ppm

EXAMPLE 27

1,2-dibenzyl-3,4-dimethyl-1,2,5,6-tetrahydropyridine oxalate 2 g of 1-phenyl-2-(N-benzyl)amino-3,4-dimethyl-6-methoxy-3-hexene obtained according to the procedure described in Example 12 is dissolved in 10 ml of carbon disulfide. 2 g of anhydrous aluminum bromide is added to the solution. The mixture is stirred at 20° – 30°C for one hour. The solvent is removed by distillation and to the residue is added an ice-cooled aqueous ammonia. Extraction is carried out with chloroform. The chloroform layer is separated, washed with water and dried with sodium sulfate. The solvent is removed by distillation under reduced pressure. The residue is subjected to distillation under reduced pressure of 0.1 mm Hg. Fractions distilled at a bath temperature of 180° to 250°C is collected to obtain 0.7 g of distillate. The distillate is dissolved in acetone. Oxalic acid is added to the soslution. As the result, the oxalate of 1,2-dibenzyl-3,4-dimethyl-1,2,5,6-tetrahydropyridine having a melting point of 177° – 180°C is obtained. Similar results to those of Example 26 are obtained by elementary analysis and NMR spectrum of the product.

EXAMPLE 28

1,2-dibenzyl-3,4-dimethyl-1,2,5,6-tetrahydropyridine oxalate 10 ml of 48% hydrobromic acid is added to 1 g of 1-phenyl-2-(N-benzyl)amino-3,4-dimethyl-6-ethoxy-3-hexene obtained according to the procedure described in Example 13 and the mixture is refluxed for 5 minutes. After cooling, the mixture is neutralized with an aqueous ammonia and extracted with ethyl ether. The ether layer is washed with water and dried with sodium sulfate. The solvent is removed by distillation. The residue is dissolved in 10 ml of acetone. 1 g of sodium hydrogen carbonate is added to the solution and refluxed for 5 hours. Insoluble matters are removed by filtration. The solvent is distilled off. The residue is purified by a silica gel chromatography using chloroform, methanol and acetic acid (90:10:5). As the result, 0.2 g of 1,2-dibenzyl-3,4-dimethyl-1,2,5,6-tetrahydropyridine is obtained. The free amine is dissolved in acetone and oxalic acid is added to the solution to obtain the oxalate of 1,2-dibenzyl-3,4-dimethyl-1,2,5,6-tetrahydropyridine.

Melting point: 178° – 180°C

EXAMPLE 29

1-benzyl-2-(p-hydroxy)benzyl-3,4-dimethyl-1,2,5,6-tetrahydropyridine oxalate

The procedure described in Example 25 is repeated except that 1(p-methoxy)phenyl-2-(N-benzyl)amino-3,4-dimethyl-6-ethoxy-3-hexene obtained in Example 14 is used in place of 1-(p-methoxy)phenyl-2-(N-benzyl)amino-3,4-dimethyl-6-methoxy-3-hexene. As the result, the oxalate of 1-benzyl-2-(p-hydroxy)benzyl-3,4-dimethyl-1,2,5,6-tetrahydropyridine is obtained.

Melting point: 123° – 125°C,

Elementary analysis,

Calculated for $C_{23}H_{27}NO_5$: C, 69.50%; H, 6.85%; N, 3.52%,

Found: C, 69.73%; H, 6.56%; N, 3.63%.

What we claim is:

1. A compound represented by the formula:

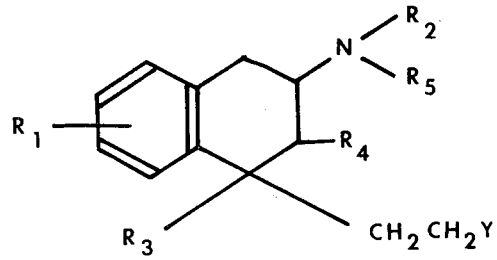

wherein $R_1$ is a hydrogen atom, a hydroxy group, an alkyl group having 1 to 4 carbon atoms, an alkoxy group having 1 to 4 carbon atoms, a benzyloxy group or an alkanoyloxy group having 1 to 4 carbon atoms; $R_2$ is a hydrogen atom, an alkyl group having 1 to 8 carbon atoms which is either substituted or unsubstituted, the substituent being a phenyl group, a benzoyl group,

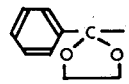

group, =O group or

group, a cycloalky group having 3 to 6 carbon atoms, a cycloalkylalkyl group having 4 to 8 carbon atoms or an alkenyl group having 3 to 8 carbon atoms which is either substituted or unsubstituted, the substituent being a chlorine atom or a bromine atom; $R_3$ and $R_4$ are the same or different and are alkyl groups having 1 to 4 carbon atoms; $R_5$ is a hydrogen atom or a benzyl group; and Y is an alkoxy group having 1 to 4 carbon atoms, a phenoxy group or a benzyloxy group.

2. A compound according to claim 1, namely 1,2,3,4-tetrahydro-2-(N-methyl)amino-3,4-dimethyl-4-(β-ethoxy)ethylnaphthalene.

3. A compound according to claim 1, namely 1,2,3,4-tetrahydro-2-(N-methyl)amino-3,4-dimethyl-4-(β-methoxy)-ethylnaphthalene.

4. The compound according to claim 1, namely 1,2,3,4-tetrahydro-2-(N-methyl)amino-3,4-dimethyl-4-(β-ethoxy)ethyl-6-methoxynaphthalene.

\* \* \* \* \*